United States Patent [19]

Nielsen et al.

[11] 4,074,434

[45] Feb. 21, 1978

[54] PRESSURE-RESPONSIVE SPEED CONTROL FOR DENTAL HANDPIECES

[75] Inventors: Milton R. Nielsen, Melrose Park; Robert A. Olsen, Palatine, both of Ill.

[73] Assignee: American Hospital Supply Corporation, Evanston, Ill.

[21] Appl. No.: 657,358

[22] Filed: Feb. 12, 1976

Related U.S. Application Data

[63] Continuation-in-part of Ser. No. 262,095, June 12, 1972, abandoned.

[51] Int. Cl.² .............................................. A61C 1/10
[52] U.S. Cl. ...................................................... 32/27
[58] Field of Search ............................... 32/27, 26, 22

[56] References Cited

U.S. PATENT DOCUMENTS

| | | | |
|---|---|---|---|
| 3,568,318 | 3/1971 | Martin | 32/27 |
| 3,842,504 | 10/1974 | Ricks | 32/27 |

*Primary Examiner*—Robert Peshock
*Attorney, Agent, or Firm*—Tilton, Fallon, Lungmus & Chestnut

[57] ABSTRACT

A speed control system for dental handpieces in which a sleeve or tube of pliable material defines an elongated deformable passage. The passage communicates at one end with a source of gas (air) under pressure and, at its opposite end, is vented to discharge a continuous stream of gas whenever the unit is in operation. When the resilient sleeve is squeezed anywhere along its length, back pressure is created which acts upon a pressure-responsive pilot valve, the pilot valve in turn regulating the speed of the dental handpiece in accordance with the amount of back pressure developed.

16 Claims, 10 Drawing Figures

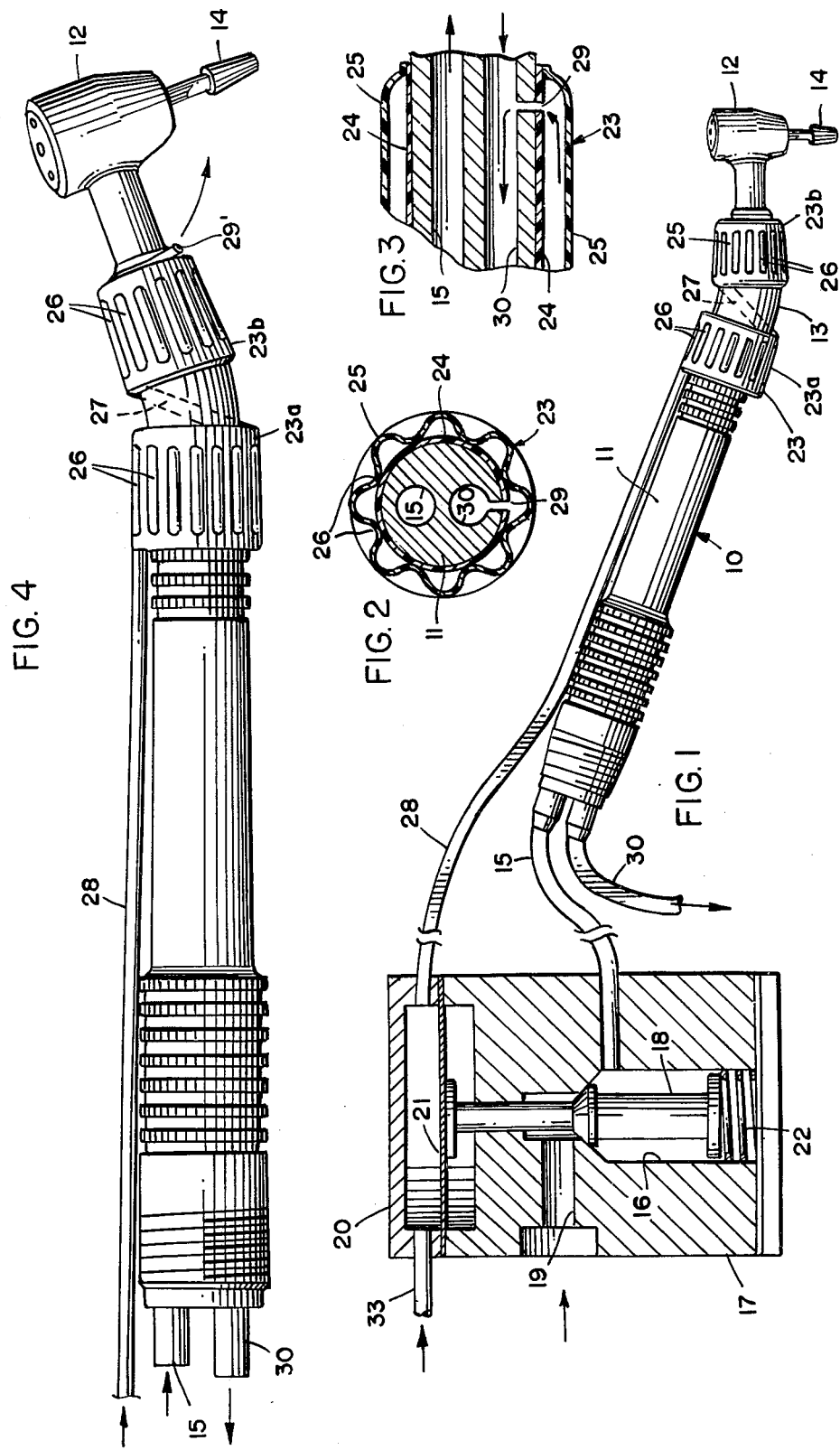

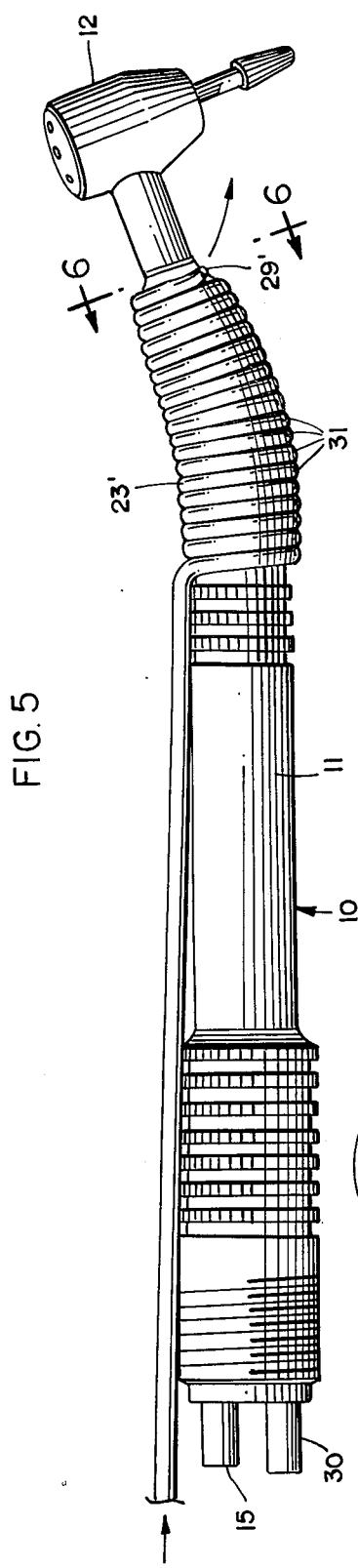
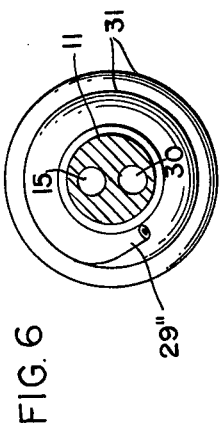
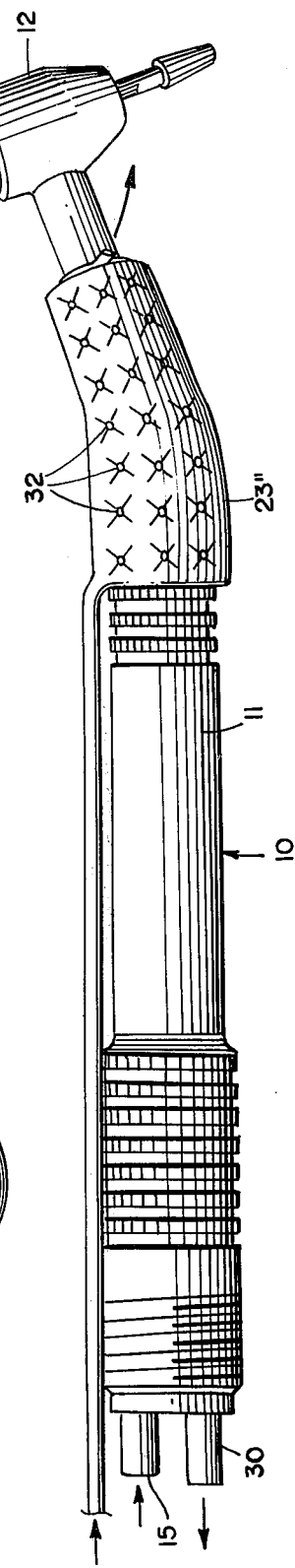

PRESSURE-RESPONSIVE SPEED CONTROL FOR DENTAL HANDPIECES

RELATED APPLICATION

This application is a continuation-in-part of our copending application Ser. No. 262,095, filed June 12, 1972 and now abandoned.

BACKGROUND

It has been known, as disclosed in Melvin D. Ricks U.S. Pat. No. 3,842,504, issued Oct. 22, 1974, to provide a turbine-driven dental handpiece with a pliant chamber extending about the handle thereof, or along a floor surface adjacent to a dental chair, such chamber being completely sealed except for its communication with a conduit leading to pressure-responsive means for controlling the flow of drive air to the handpiece. A fluid, which would ordinarily be non-compressible and therefore a liquid rather than a gas, is contained within the chamber and conduit leading to the pressure-responsive control means. When the pliant chamber is squeezed, the liquid is displaced along the conduit and into the control means which in turn regulates the flow of drive air to the turbine of the handpiece. The extent to which the pliant chamber is compressed determines the extent of liquid displacement and, consequently, the operating speed of the handpiece.

While such a construction provides the advantages of direct fingertip or foot control of the handpiece speed, it has the disadvantages of being highly sensitive to leaks and to temperature and pressure changes. The effectiveness of such a system depends on the use of a sealed chamber from which the fluid is displaced as the chamber is reduced in size. Quite obviously, a loss of fluid would adversely affect the operation of the unit, just as the loss of fluid in any sealed hydraulic system would be expected to have adverse consequences. Since such a fluid would in most instances be a liquid, the escape of such fluid, by leakage or diffusion, might also result in the formation of an objectionable surface film on the instrument, cause staining and other damage to clothing and equipment, and produce other undesirable results in addition to loss of handpiece speed control.

In addition the need to prevent leakage from such a system requires the use of elements designed to insure positive sealing and such elements, when they are appended to the dental handpiece itself, are undesirable to the extent that they intend to increase weight in a handpiece which must be manipulated with great precision and sensitivity. Since such a system practically necessitates the use of a liquid (i.e., non-compressible) medium, the weight of such medium in a dental handpiece is a further disadvantage.

Other disadvantages may also be present. Thus, unintentional operation of the handpiece might occur simply by reason of thermal expansion of the fluid within the sealed system. Also, where the system utilizes fingertip control of handpiece speed, the provision of an additional liquid-filled conduit within the hose leading to the handpiece would be expected to add further bulk, weight, and stiffness, thereby making manipulation of the handpiece more difficult.

Other patents revealing the state of the art are U.S. Pat. Nos. 1,078,785, 2,591,119, 3,032,878, 3,125,809, 3,277,254, 2,204,644, 2,787,756, 2,937,444, 2,622,619, 3,188,011, 3,568,318, 3,250,005, 3,256,603, 3,346,958 and 3,676,931.

SUMMARY

An important aspect of the present invention lies in the discovery that the disadvantages inherent in the construction and operation of the aforementioned prior devices may be overcome by utilizing a compressible (gaseous) fluid medium and continuously bleeding such fluid from the system at or near the end of the elongated pliant sleeve. The pliant sleeve or chamber therefore serves as a compressible conduit between the source of gas supply and the point of gas discharge. While it is important that the chamber normally be maintained under at least slight positive internal pressure, and while the bleed outlet may be reduced in size to increase such internal pressure when needed, it has been found that the normal resistance to flow of gas through the elongated pliant chamber may produce sufficient positive pressure within the chamber to make reduction in the size of the outlet unnecessary. Squeezing of the pliant chamber anywhere along its length reduces its internal cross section at that point and, in effect, creates a temporary orifice at the selected point. The increased pressure on the inlet side, that is, the back pressure, is used to operate a suitable pressure-responsive valve which modulates the flow of drive air to the handpiece in relation to the size of the variable and transient orifice. In contrast to the closed system heretofore described, the open or continuously bleeding system of this invention is substantially insensitive to minor leakage. For example, diffusion of gas through the wall of the pliant chamber or tube presents no problem in this system, whereas diffusion in a closed system would normally require recharging and might require other periodic maintenance operations. Leaks which would not greatly reduce pressure within the chamber of the open system would have no material effect on its operation whereas similar leaks in a closed system would be expected to render the entire unit inoperative. Furthermore, because of the difference in the fluid medium (gas vs. liquid) leakage should it occur in this system would not present the clean-up problems posed by a system utilizing a liquid.

Of particular importance is the fact that an open or bleeding system is not sensitive to changes in temperature, whereas a closed system is susceptible to fluid expansion and contraction in response to external (and internal) temperature fluctuations.

Since continuous leakage is an essential feature of the open system, and since the fluid medium is a gas, preferably air, the system permits the construction of a fingertip control for a dental handpiece while at the same time providing a handpiece construction which is relatively light in weight. Apart from the differences in weight resulting directly from the use of gas instead of a liquid, the open system requires fewer elements which are intended to insure against leakage and which would necessarily add weight to the unit as a whole.

The elongated pliant chamber or sleeve may be disposed in any location where it may be conveniently squeezed at any point along its length to regulate handpiece speed. Where fingertip speed control is desired, the chamber may be disposed along the handle of the handpiece; where foot control is preferred, the elongated chamber or sleeve may extend along the floor on or near the base of the dental chair. Force concentrating means in the form of ribs or undulations may extend across the sleeve to localize and thereby assist in the formation of a variable speed-controlling orifice without requiring the application of excessive force by the operator.

DRAWINGS

FIG. 1 is a side elevational view of a handpiece equipped with the speed control means of the present invention, the handpiece being illustrated in conjunction with a pressure-responsive pilot valve represented in vertical section.

FIG. 2 is an enlarged cross sectional view taken along line 2—2 of FIG. 1.

FIG. 3 is an enlarged broken longitudinal sectional view taken along line 3—3 of FIG. 2.

FIG. 4 is a perspective view illustrating a second embodiment of the invention.

FIG. 5 is a perspective view illustrating a third embodiment.

FIG. 6 is an enlarged sectional view taken along line 6—6 of FIG. 5.

FIG. 7 is a perspective view illustrating a fourth embodiment of the invention.

DESCRIPTION

Figure 8:
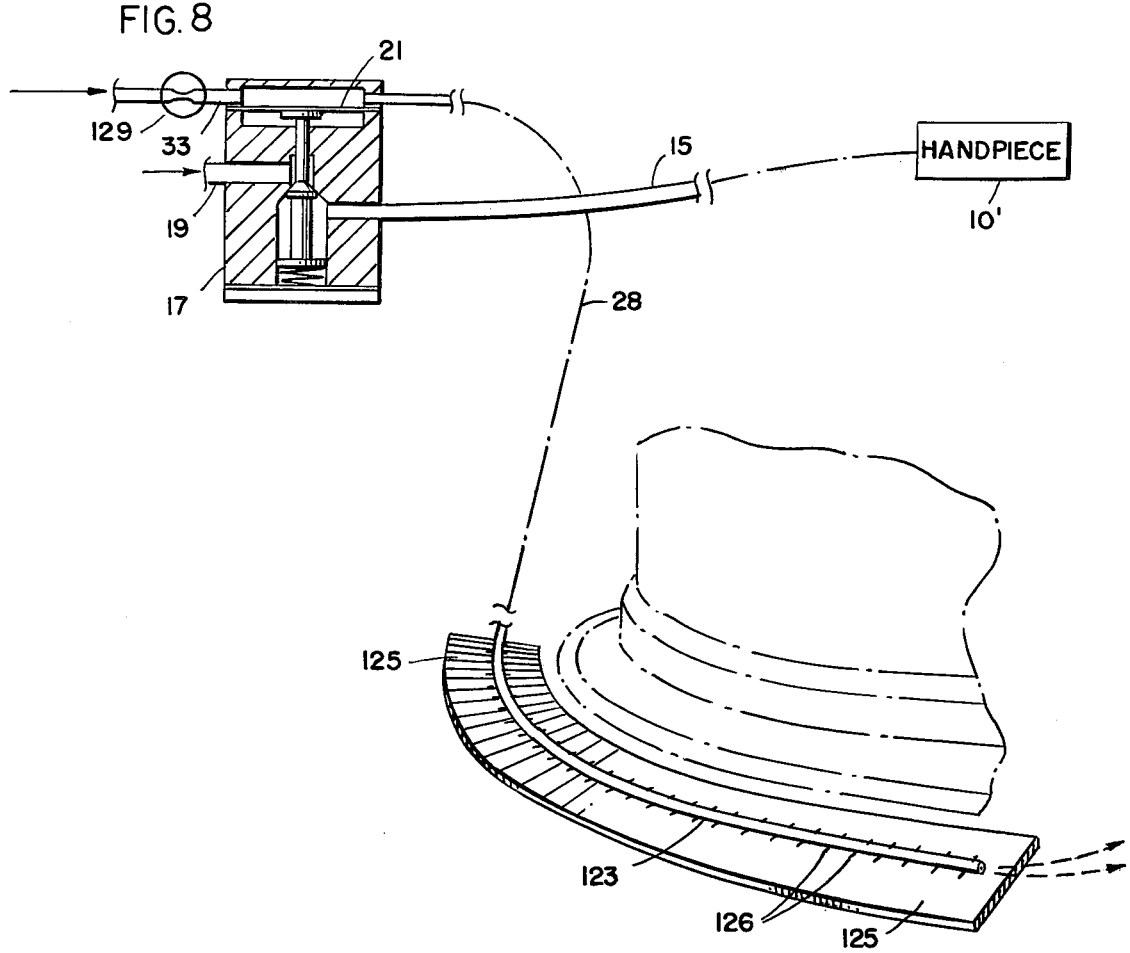
FIG. 8 is a schematic view of a handpiece speed control system in which the pliant chamber extends along the floor near a dental chair.

FIG. 1 illustrates a dental handpiece 10 having an elongated handle 11 and a workhead 12. In the particular illustration given, the handpiece is of the contra angle type with an angular bend at 13, all as well known in the art. The workhead contains an air turbine, the rotor of the turbine carrying a conventional dental bur 14. In general construction and operation, apart from the speed-control system hereinafter described, the handpiece may be similar to the one shown and described in co-owned Staunt U.S. Pat. No. 3,325,899. It is to be understood, however, that the speed-control system is not limited to air-driven handpieces of the contra angle type and that it may be used in conjunction with other well known types of handpieces, although preferably those which are powered by an air motor or turbine.

Drive air is supplied to the workhead by passage means in the form of conduit 15. As shown in FIG. 1, the conduit communicates with chamber 16 of a pilot valve casing 17. A valve member 18 is movable within chamber 16 between the closed position illustrated in FIG. 1 and an open position. When the valve is open, drive air from a suitable source (not shown) flows through passage 19, chamber 16, and passage means 15 into workhead 12 to drive the turbine rotor.

Air under pressure is also supplied to pressure-responsive means in the form of diaphragm chamber 20 and flexible diaphragm 21. A spring 22 normally biases valve member 18 to its closed position with diaphragm 21 in a raised or generally planar condition. Should pressure in the diaphragm chamber exceed the upward force exerted by spring 22, the diaphragm 21 will flex downwardly to shift the valve member 18 into an open position.

A pliant chamber 23 extends about a substantial portion of the length of handle 11 in close proximity to workhead 12. In the embodiment illustrated in FIGS. 1-3, the chamber comprises a pair of double-layered sleeves 23a and 23b disposed adjacent elbow 13. Each sleeve is generally annular in configuration and, as illustrated most clearly in FIGS. 2 and 3, is formed of inner and outer walls 24 and 25. The inner wall fits snugly about handle 10 and may be cemented or otherwise secured thereto. The outer wall is spaced outwardly from the inner wall although, in the illustration given, the two walls are sealed together along circumferentially-spaced parallel lines of contact 26 to limit the extent of outward flexure of wall 25. Because of the limited length of lines of contact 26, however, all portions of the space between walls 24 and 25 communicate with each other. Furthermore, the two sleeves 23a and 23b are in direct communication by means of connecting passage 27.

One end of the two-section pliant chamber 23, preferably the end farthest from workhead 12, is provided with an inlet which communicates directly with air supply line 28, the other end of the supply line communicating with diaphragm chamber 20. The opposite end of the pliant chamber —that is, the end nearest workhead 12 — is provided with a bleed port or outlet 29. In the form of the invention illustrated in FIGS. 1-3, bleed port 29 communicates directly with an internal exhaust passage 30 which passes longitudinally through handle 10 and which carries exhaust air used in driving the turbine. In the illustration given, bleed port 29 is of reduced cross section in order to increase slightly the positive pressure within the pliant chamber; however, it should be understood that sufficient positive pressure may be generated even if the port or outlet is of the same cross sectional dimensions as those of the remainder of the chamber, and that tube length, lumen diameter, and flow rate may all be varied to produce a pliant chamber which exerts slight but definite resistance to squeezing force applied by the fingers.

The embodiment illustrated in FIG. 4 is identical to the one already described except for the bleeding port or outlet 29' is directed outwardly or externally instead of discharging bleed air into the return passage 15 of the handpiece. External discharge may be less desirable because of noise and possible discomfort or distraction from the continuous discharge of air; however, such disadvantages, if they exist, would be minimized by inflating the pliant chamber with air at relatively low positive pressure, or by introducing a suitable flow restriction or flow control orifice in the line 33 upstream of pilot valve assembly 17, thereby keeping the volume and rate of discharge from the bleed port at relatively low levels. A flow restrictor would have the additional advantage of increasing the pressure drop upstream of the pliant chamber, thereby increasing the control pressure differential and sensitivity of the system as a whole.

The embodiments of FIGS. 5 and 6 is identical to the one illustrated in FIG. 4 except for the pliant chamber 23' is formed of multiple spirally wound coils 31 of resilient tubing. The coils may be bonded to each other and may be cemented or otherwise secured to the handle 11 of the handpiece. The bleed portion 29" discharges externally; however, internal discharge in the manner described in connection with the embodiment of FIGS. 1-3 may of course be utilized.

FIG. 7 illustrates a pliant chamber 23" which is similar to the chamber of FIG. 4 except that a single uninterrupted section is provided (rather than double sections connected by passage means 27). There is also a further difference in the spaced connections between the inner and outer walls of the chamber. Specifically, the inner and outer walls are heat sealed (or heat stitched) or otherwise secured together at spaced points 32 (FIG. 7) rather than along lines 26 (FIG. 1). In other respects, the two forms are the same.

Figure 9:
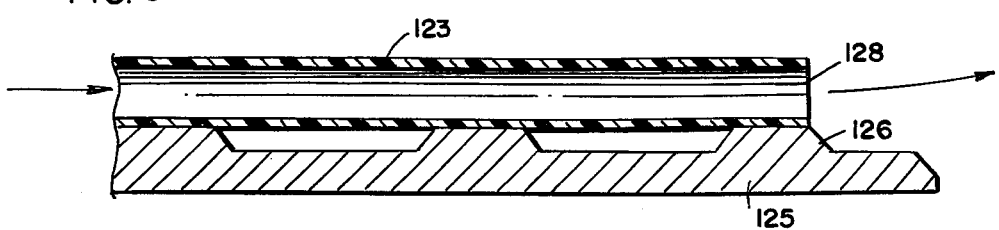
FIG. 9 is an enlarged longitudinal sectional view showing the discharge end of the pliant chamber of FIG. 8.
Figure 10:
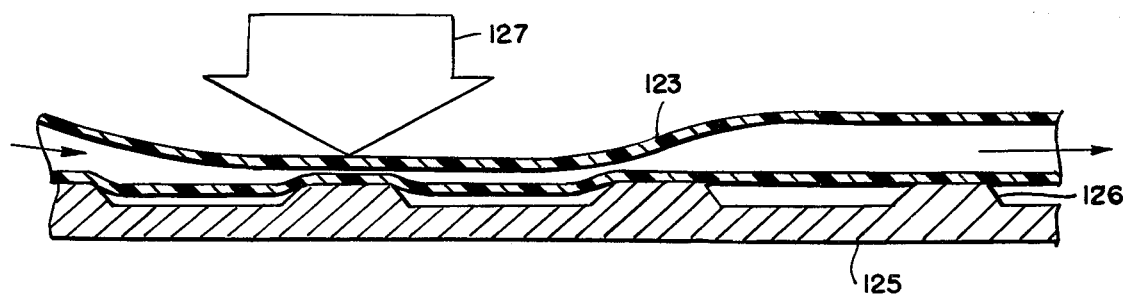
FIG. 10 is a sectional view showing an intermediate portion of the pliant chamber as it is squeezed by the application of foot pressure.

In the embodiment of FIGS. 8-10 the pliant chamber 123 takes the form of a resilient tube extending along the floor adjacent the base of a dental chair. The elongated pliant tube may be formed integrally with, or may be adhesively secured to (as shown), a suitable mat or support member 125. As shown, the mat and tube are curved to follow generally the perimetric outline of the base 124, the tube extending a substantial angular distance along the circumference of the base. Transverse ribs 126 extend externally of the pliant chamber (in the illustrated embodiment they are displaced beneath the chamber and are formed as part of the mat; however, they may instead be disposed above the chamber and, in any event, be formed in the exterior wall portion of the tube itself) so as to localize or concentrate the collapsing force applied to the tube when the operator exerts a downward force with his foot as indicated by arrow 127 (FIG. 10). It will be observed from FIG. 9 that the outlet 128 for the pliant chamber or tube is of the same cross sectional dimensions as the lumen of that tube; however, it is to be understood that the bleed outlet port may if desired be reduced in size to increase the positive pressure within the pliant chamber.

The diaphragm valve assembly 17 depicted in FIG. 8 is the same as already described in connection with the other embodiments. A suitable flow restriction 129 is located in passage 33 upstream of the valve assembly to create a greater initial pressure drop or to reduce flow rates. Line 15 carries drive air to the dental handpiece 10' which may be identical to handpiece 10 except for the omission of the fingertip speed control means.

The walls of the pliant chamber in each of the forms described above may be formed of plastic, rubber, or any other materials having the properties of flexibility, durability, impermeability, and chemical inertness. The preferred fluid is air although other gases, or mixtures of gases, may be used. Air is particularly suitable because the turbine driven handpieces are air-powered. Thus, the source which supplies drive air to passage 19 of the casing 17 may also supply air to passage 33 for the diaphragm chamber.

In operation, a squeezing force applied to the pliant chamber either by the fingers (in the forms of FIGS. 1-7) or by foot (in the form of FIGS. 8-10) increases the pressure drop between the inlet and outlet of that chamber and increases the pressure above diaphragm 21, thereby shifting the pilot valve into a lowered or opened position. The extent of valve movement is dependent on the amount of squeezing force applied to the pliant chamber. Therefore, the speed of the handpiece may be controlled by varying the extent to which the pliant chamber or tube is compressed.

A particularly important aspect of the invention lies in the fact that operation of the pilot valve is brought about because of changes in the pressure drop between the inlet and outlet of the pliant chamber and, consequently, a relatively quick response in valve operation is achieved in contrast to prior units in which an appreciable time lag may occur before fluid is displaced from one chamber to another to operate the valve. It is believed especially significant that reasonably fast response is obtained in the embodiments of the present invention despite the fact that a compressible (i.e., gaseous) fluid is utilized.

While in the foregoing several embodiments of the invention have been disclosed in considerable detail for purposes of illustration, it will be understood by those skilled in the art that many of these details may be varied without departing from the spirit and scope of the invention.

We claim:

1. A pressure-responsive speed control system for dental handpieces comprising a dental handpiece having a workhead, an elongated pliant chamber having an exposed wall portion capable of being squeezed by an operator to reduce the internal cross section of said chamber, said chamber having an inlet communicating with a gas supply line and with pressure-responsive means, said pressure-responsive means being operatively connected to said handpiece for controlling the operating speed of said workhead, said chamber also having an outlet spaced a substantial distance along the length of said chamber from said inlet for bleeding gas from said chamber during operation of said speed control system.

2. The system of claim 1 in which said dental handpiece also includes an elongated handle, said pliant chamber being mounted on said handle with said exposed wall portion adapted to be squeezed between the fingers when said handpiece is held by an operator.

3. The system of claim 2 in which said outlet of said pliant chamber discharges externally of said handpiece.

4. The system of claim 2 in which said handle is provided with a gas discharge passage extending therealong, said outlet of said pliant chamber communicating with said discharge passage.

5. The system of claim 2 in which said workhead includes an air-driven motor, passage means along said handle for supplying driven air to said motor, said pressure-responsive means communicating with said passage means for regulating drive air to said workhead and for varying the speed of said motor in response to changes in pressure drop within said chamber.

6. The system of claim 2 in which said pliant chamber is annular in cross section and includes inner and outer walls normally maintained in spaced relation by gas supplied by said supply line.

7. The system of claim 6 in which said walls are secured together at a plurality of spaced points.

8. The system of claim 6 in which said walls are secured together along a plurality of spaced lines.

9. The system of claim 2 in which said pliant chamber is composed of a multiplicity of coils of resilient tubing extending about a portion of said handpiece handle.

10. The system of claim 1 in which said elongated pliant chamber is adapted to extend along a floor surface, said exposed wall portion being engagable by the foot of an operator for reducing the internal cross sectional dimensions of said chamber and for producing a variable orifice within said chamber, thereby varying the gas pressure applied to said pressure-responsive means.

11. The system of claim 10 in which said workhead includes an air-driven motor, passage means for supplying drive air to said motor, said pressure-responsive means communicating with said passage means for regulating drive air to said workhead and for varying the speed of said motor in response to changes in the size of the variable orifice formed within said pliant chamber in response to squeezing force applied thereto by an operator's foot.

12. The system of claim 10 in which a support member is disposed beneath said pliant chamber for supporting said chamber upon a floor surface.

13. The system of claim 12 in which transversely-extending force-concentrating ribs are disposed externally of said pliant chamber, said ribs being spaced along the length of said elongated pliant chamber for localizing deformation of said chamber in response to squeezing force applied by the foot of an operator.

14. An assembly for use in controlling the speed of a dental handpiece, comprising an elongated pliant chamber adapted to be supported upon a floor surface, said chamber having an inlet and an outlet at opposite ends thereof and having a deformable imperforate tubular wall extending therebetween, pressure-responsive means adapted to be connected to a dental handpiece for varying the operating speed of said handpiece in response to changes in air pressure applied to said pressure-responsive means, said pressure-responsive means also being adapted for connection to a source of air under pressure, and conduit means for conducting a stream of air from said pressure-responsive means to said inlet of said pliant chamber, said pliant chamber being deformable by the application and removal of compressive force applied by an operator's foot at any point along the length of said tubular wall to produce a variable orifice within said chamber at that point, thereby altering the pressure applied to said pressure-responsive means and varying the operating speed of said handpiece.

15. The system of claim 14 in which a plurality of ribs are disposed externally of the deformable imperforate tubular wall of said pliant chamber and extend transversely in longitudinally-spaced series therealong for localizing deformation of said chamber in response to a squeezing force applied by an operator's foot.

16. The system of claim 14 in which flow-reducing means is in flow communication with said pressure-responsive means for reducing the flow of air thereto.

* * * * *